United States Patent [19]

Drent

[11] Patent Number: 4,642,371

[45] Date of Patent: Feb. 10, 1987

[54] PROCESS FOR THE PREPARATION OF DIESTERS OF DICARBOXYLIC ACIDS

[75] Inventor: Eit Drent, Amsterdam, Netherlands

[73] Assignee: Shell Oil Company, Houston, Tex.

[21] Appl. No.: 862,928

[22] Filed: May 14, 1986

[30] Foreign Application Priority Data

Jun. 14, 1985 [GB] United Kingdom ............... 8515140

[51] Int. Cl.$^4$ .............................................. C07C 67/38
[52] U.S. Cl. ..................................... 560/114; 560/97; 560/204
[58] Field of Search ......................... 560/114, 97, 204

[56] References Cited

U.S. PATENT DOCUMENTS

| | | | |
|---|---|---|---|
| 4,138,580 | 2/1979 | Umemura et al. | 560/81 |
| 4,234,740 | 11/1980 | Umemura et al. | 560/81 |
| 4,260,810 | 4/1981 | Umemura et al. | 560/204 |

*Primary Examiner*—Michael L. Shippen

[57] ABSTRACT

Preparation of a diester of a dicarboxylic acid by reacting an unsaturated hydrocarbon having two carbon atoms less than the dicarboxylic acid, carbon monoxide and a nitrite ester with a solvent in the presence of a catalyst system formed by combining (1) a Group VIII noble metal compound and (2) a vanadium salt and/or a titanium salt.

9 Claims, No Drawings

4,642,371

PROCESS FOR THE PREPARATION OF DIESTERS OF DICARBOXYLIC ACIDS

FIELD OF THE INVENTION

The invention relates to a process for the preparation of a diester of a dicarboxylic acid, the acid having two more carbon atoms than the unsaturated hydrocarbon used as a starting material.

BACKGROUND OF THE INVENTION

It is known from German Patent Application No. 2,853,178 to prepare diesters of dicarboxylic acids, the acid having two more carbon atoms than the unsaturated hydrocarbon used as a starting material by reacting an unsaturated hydrocarbon, carbon monoxide, an alcohol and an ester of nitrous acid in the presence of a compound of a metal of the platinum group and of a metal halide. Example 37 of this German Application shows that the desired diester was obtained in a relatively low yield, calculated on starting nitrite ester.

The Applicants have now found that by replacing this metal halide with a salt to be specified hereinafter a particularly high yield of the said diesters is obtained.

SUMMARY OF THE INVENTION

This invention relates to a process for the preparation of a diester of a dicarboxylic acid, the acid having two more carbon atoms then the unsaturated hydrocarbon used as a starting material, which process comprises causing an unsaturated hydrocarbon, carbon monoxide and an ester of nitrous acid to react in the presence of a solvent and a catalytic system formed by combining (a) a compound of a noble metal of Group VIII of the Periodic Table of the Elements and (b) a vanadium salt and/or a titanium salt.

DESCRIPTION OF THE PREFERRED EMBODIMENTS

The unsaturated hydrocarbon may be an ethylenically unsaturated compound or an acetylenically unsaturated compound. Preference is given to alkenes having in the range of from 2 to 20 carbon atoms per molecule and to cycloalkenes having up to 20 carbon atoms per molecule, particularly to ethene, propene, 1-butene and 2-butene. Other examples of suitable alkenes are pentene, hexene, heptene, octene, nonene, decene, undecene, dodecene, tridecene, tetradecene, pentadecene, hexadecene, heptadecene, octadecene, nonadecene and eicosene. Examples of suitable cycloalkenes are cyclopentene, cyclohexene, cycloheptene, cyclooctene, indene and phenalene. Other examples of suitable starting unsaturated compounds are styrene, allylbenzene, allene, 1,2-butadiene, 1,3-butadiene, the pentadienes, the hexadienes, the cyclopentadienes, acetylene and propyne.

Examples of suitable esters of nitrous acid are esters of nitrous acid with aliphatic, cycloaliphatic or aromatic alcohols. Preference is given to esters of nitrous acid with an alkanol having in the range of from 1 to 8 carbon atoms per molecule, for example, methanol, ethanol, propanol, 2-propanol, butanol, 2-butanol, tert-butyl alcohol, pentanol, 2-pentanol, hexanol, heptanol and octanol. Other examples of suitable alcohols are cyclohexanol, 2-methylcyclohexanol, ethylene glycol, glycerol, phenol, the cresols, the xylenols and the naphthols. Very good results have been obtained with butyl nitrite. The ester of nitrous acid may be formed in situ, for example by reaction of an alcohol with an oxide of nitrogen or with nitric acid. Examples of suitable oxides of nitrogen are NO, $N_2O_3$, $N_2O_4$ and $N_2O_5$. The use of NO, preferably in combination with molecular oxygen, is preferred. The molecular oxygen may be introduced into the reaction mixture as, for example, pure oxygen or oxygen diluted with an inert gas, such as air or air enriched with oxygen.

The compounds of noble metals of Group VIII of the Periodic Table of the Elements which may be used are compounds of platinum, palladium, rhodium, osmium, iridium and ruthenium. Very good results have been obtained with palladium compounds. Examples of suitable salts of noble metals are nitrates, sulfates, halides (fluorides, chlorides, bromides and iodides) and carboxylates, preferably alkanoates derived from alkanoic acids having not more than 12 carbon atoms per molecule. Very good results have been obtained with palladium chloride. Mixtures of compounds of two noble metals may be used, for example of platinum and palladium.

Further examples of suitable palladium compounds are palladium complexes such as bis(2,4-pentanedionato)palladium, bis(picolinato)palladium, tetrakis(triphenylphosphine)palladium, tetrakisacetonitrile palladium tetrafluoroborate, bis(tri-o-tolylphosphine)palladium acetate, bis(triphenylphosphine)palladium sulfate, palladium olefin complexes, for instance di-$\mu$-chloro-dichlorobis(ethylene)dipalladium ($[Pd.C_2H_4.ClH2]_2$) and di-$\mu$-chloro-dichlorobis(propylene)dipalladium ($[Pd.C_3H_6.Cl_2]_2$), and palladiumhydride complexes.

The vanadium salts and titanium salts are surprisingly effective in accelerating the formation of the desired diesters. When the process according to the invention is modified by replacing these salts with, for example, a cupric salt, a considerably lower selectively to these desired esters is found, large amounts of diesters of oxalic acid being formed.

Examples of suitable salts of vanadium and titanium are chlorides, nitrates, sulfates and carboxylates, preferably alkanoates derived from alkanoic acids having not more than 12 carbon atoms per molecule. Very good results have been obtained with vanadium(III) chloride and titanium(IV) chloride.

The molar ratio of unsaturated hydrocarbon to carbon monoxide may vary within wide limits and is preferably in the range of from 0.2 to 10. It is a feature of the present invention that this molar ratio can be kept low, for example in the range of from 1 to 5, thus avoiding recycling large amounts of unreacted unsaturated compound.

The molar ratio of unsaturate hydrocarbon to ester of nitrous acid may vary within wide limits, suitably between 0.1 and 20 and preferably between 0.5 and 5. The molar ratio of ester of nitrous acid to noble metal of Group VIII of the Period Table of the Elements may also vary within wide limits and is suitable between 10 and 100,000.

The molar ratio of vanadium salt and/or titanium salt to noble metal of Group VIII may vary within wide limits and is suitably between 0.1 and 100.

The process according to the present invention can be carried out in wide ranges of temperature and pressure, preferably in the range of from 20° C. to 200° C., more preferably from 50° C. to 125° C., and in the range of from 5 to 200 bar, more preferably from 10 to 100 bar.

The process according to the invention is carried out in the presence of a solvent, for example, an alkanol such as those having 1 to 8 carbon atoms per molecule. Preference is given to the alkanol from which the ester of nitrous acid is derived. Other examples of suitable solvents are ethers, such as methyl ethyl ester, diethyl ether, dipropyl ether, tetrahydrofuran, dimethyl ether of diethylene glycol (also referred to as "diglyme"), methyl tert-butyl ether or 1,4-dioxane; halongenated hydrocarbons such as chloroform, chlorobenzene or perfluoroalkanes; ketones such as acetone, diethyl ketone or methyl isobutyl ketone; esters such as methyl formiate, ethyl formiate, propyl formiate, methyl acetate, ethyl acetate, propyle acetate and methyl or ethyl esters of adipic acid, succinic acid, maleic acid, fumaric acid, propionic acid, oxialic acid and benzoic acid; sulfones such as dimethyl sulfone, methyl butyl sulfone and tetrahydrothiophene 1,1-dioxide (also referred to as "sulfolane"); sulfoxides such as dimethyl sulfoxide and diethyl sulfoxide; aromatic hydrocarbons such as benzene, toluene and the xylenes; cycloalkanes such as cyclohexane; nitrobenzene.

The process according to the invention can be carried out batchwise, semi-continuously or continuously. The reaction time may vary in relation to the temperature used, between 0.5 and 20 hours.

The following Examples are intended to illustrate the invention and are not to be construed as limiting the scope of the invention. The experiments were carried out in a 300 ml autoclave made of Hastelloy C ("Hastelloy" is a trademark) provided with a magnetically driven stirrer. The autoclave was charged with butyl nitrite and then with ethylene and carbon monoxide until their partial pressures were 30 and 20 bar, respectively. Then, the autoclave was heated to a temperature of 70° C. and kept at this value for 5 h, followed by determining the conversion of butyl nitrite and the selectivities to dibutyl succinate and dibutyl oxalate. The selectivity to a certain compound, expressed in a percentage, is defined herein as $$(a/b) \times 100$$

in which "a" is the amount of starting compound that has been converted into that certain compound and "b" is the total amount of starting compound that has been converted.

EXAMPLE 1

The autoclave was charged with butanol (20 ml), butyl nitrite (30 ml), palladium(II) chloride (0.1 mmol) and vanadium(III) chloride (2 mmol), the molar ratio ethylene to butyl nitrite being 1.1 and that of butyl nitrite to palladium(II) chloride being 2200. The conversion of butyl nitrite was 80% and the selectivities to dibutyl succinate and dibutyl oxalate were 80% and 10% respectively.

COMPARATIVE EXPERIMENT A

An experiment was run in the same manner as Example 1, except that 20 ml of butyl nitrite and 30 ml of butanol were used and that the vanadium(III) chloride was not added. Only a trace of reaction products was found.

COMPARATIVE EXPERIMENT B

An experiment was run in the same manner as Example 1, except that the vanadium(III) chloride was replaced with 2 mmol of cupric chloride. The conversion of butyl nitrite was 90% and the selectivities to dibutyl succinate and dibutyl oxalate were 36% and 56%, respectively.

COMPARATIVE EXPERIMENT C

The autoclave was charged with butanol (30 ml), butyl nitrite (20 ml), palladium(II) tosylate (0.1 mmol) and triphenylphosphine (3 mmol). The conversion of butyl nitrite was 20% and the selectivity to dibutyl oxalate was 80%. Only traces of dibutyl succinate were found.

EXAMPLE 2

An experiment was run in the same manner as Example 1, except that the vanadium(III) chloride was replaced with 2 mmol of titanium(IV) chloride. The conversion of butyl nitrite was 70% and the selectivities to dibutyl succinate and dibutyl ocalate were 71% and 15%, respectively.

What is claimed is:

1. A process for the preparation of a diester of a dicarboxylic acid having two or more carbon atoms than the unsaturated hydrocarbon used as a starting material, which comprises reacting an unsaturated hydrocarbon, carbon monoxide and an ester of nitrous acid with a solvent in the presence of a catalytic system formed by combining (1) a compound of a noble metal of Group VIII of the Periodic Table of the Element and (b) a vanadium salt and/or a titanium salt.

2. The process of claim 1 wherein the compound of the noble metal is a palladium compound.

3. The process of claim 1 wherein the unsaturated hydrocarbon is an alkene having in the range of from 2 to 20 carbon atoms per molecule.

4. The process of claim 3 wherein the unsaturated hydrocarbon is a cycloalkene having up to 20 carbon atoms per molecule.

5. The process of claim 3 wherein the unsaturated hydrocarbon is ethene, propene, or a butene.

6. The process of claim 1 wherein the ester of nitrous acid is an ester of nitrous acid with an alkanol having in the range of from 1 to 8 carbon atoms per molecule.

7. The process of claim 6 wherein the ester is butyl nitrite.

8. The process of claim 1 wherein the vanadium salt is vanadium(III) chloride and the titanium salt is titanium(IV) chloride.

9. The process of claim 1 wherein a molar ratio unsaturated hydrocarbon to carbon monoxide in the range of from 0.2 to 2 is applied.

* * * * *